(12) United States Patent
Ghosh et al.

(10) Patent No.: US 7,713,898 B2
(45) Date of Patent: May 11, 2010

(54) METHOD OF MAKING A PHOSPHORUS-MODIFIED ZEOLITE CATALYST

(75) Inventors: Ashim Kumar Ghosh, Houston, TX (US); Neeta Kulkarni, Houston, TX (US); Pamela Harvey, Missouri City, TX (US)

(73) Assignee: Saudi Basic Industries Corporation, Riyadh (SA)

( * ) Notice: Subject to any disclaimer, the term of this patent is extended or adjusted under 35 U.S.C. 154(b) by 0 days.

(21) Appl. No.: 12/142,184

(22) Filed: Jun. 19, 2008

(65) Prior Publication Data

US 2008/0305945 A1    Dec. 11, 2008

Related U.S. Application Data

(63) Continuation of application No. 11/136,877, filed on May 25, 2005, now Pat. No. 7,399,727, which is a continuation-in-part of application No. 10/831,729, filed on Apr. 23, 2004, now Pat. No. 7,285,511.

(51) Int. Cl.
    *B01J 29/06* (2006.01)
(52) U.S. Cl. .......................... 502/77; 502/60
(58) Field of Classification Search ............ 502/60, 502/77
    See application file for complete search history.

(56) References Cited

U.S. PATENT DOCUMENTS

| | | | |
|---|---|---|---|
| 3,702,886 A | 11/1972 | Argauer et al. | |
| 3,962,364 A | 6/1976 | Young | |
| 3,965,207 A | 6/1976 | Weinstein | |
| 4,115,424 A | 9/1978 | Unland et al. | |
| 4,140,726 A | 2/1979 | Unland et al. | |
| 4,152,364 A | 5/1979 | Chu | |
| 4,250,345 A | 2/1981 | Chu | |
| 4,278,827 A | 7/1981 | Chu et al. | |
| 4,409,132 A | 10/1983 | Forbus et al. | |
| 4,420,418 A * | 12/1983 | Chu | 502/77 |
| 4,444,989 A | 4/1984 | Herkes | |
| 4,469,806 A * | 9/1984 | Forbus et al. | 502/62 |
| RE31,919 E | 6/1985 | Butter et al. | |
| 4,548,914 A | 10/1985 | Chu | |
| 4,554,394 A | 11/1985 | Forbus et al. | |
| 4,590,321 A | 5/1986 | Chu | |
| 4,623,530 A | 11/1986 | Cullo et al. | |
| 4,623,633 A | 11/1986 | Young | |
| 4,638,106 A | 1/1987 | Pieters et al. | |
| 4,665,251 A | 5/1987 | Chu | |
| 4,670,616 A | 6/1987 | De Simone et al. | |
| 4,673,767 A | 6/1987 | Nimry et al. | |
| 4,694,114 A | 9/1987 | Chu et al. | |
| 4,695,666 A | 9/1987 | Chao et al. | |
| 4,695,667 A | 9/1987 | Sumitani et al. | |
| 4,704,495 A | 11/1987 | Dessau | |
| 4,716,135 A | 12/1987 | Chen | |
| 4,721,827 A | 1/1988 | Cullo et al. | |
| 4,727,209 A | 2/1988 | Chao | |
| 4,746,763 A | 5/1988 | Kocal | |
| 4,758,328 A | 7/1988 | Young | |
| 4,761,513 A | 8/1988 | Steacy | |
| 4,781,815 A | 11/1988 | Pellet et al. | |
| 4,847,223 A | 7/1989 | Le Van Mao et al. | |
| 4,861,930 A | 8/1989 | Cottrell et al. | |
| 4,873,067 A | 10/1989 | Valyocsik et al. | |
| 4,891,197 A | 1/1990 | Derouane et al. | |
| 4,891,467 A | 1/1990 | Sikkenga | |
| 4,902,406 A | 2/1990 | Valyocsik | |
| 4,912,073 A | 3/1990 | Chu | |
| 4,914,067 A | 4/1990 | Pellet et al. | |
| 4,935,574 A | 6/1990 | D'Amore et al. | |
| 4,962,255 A | 10/1990 | Fraenkel et al. | |
| 4,973,399 A | 11/1990 | Green et al. | |
| 4,973,781 A | 11/1990 | Valyocsik et al. | |
| 4,980,052 A | 12/1990 | Green et al. | |
| 5,041,402 A | 8/1991 | Casci et al. | |
| 5,043,502 A | 8/1991 | Martindale et al. | |
| 5,047,141 A | 9/1991 | Chu | |
| 5,068,483 A | 11/1991 | Barthomeuf et al. | |
| 5,094,995 A | 3/1992 | Butt et al. | |
| 5,105,047 A | 4/1992 | Waller | |
| 5,108,579 A | 4/1992 | Casci | |
| 5,110,776 A | 5/1992 | Chitnis et al. | |
| 5,124,299 A | 6/1992 | Waller | |
| 5,171,921 A | 12/1992 | Gaffney et al. | |

(Continued)

FOREIGN PATENT DOCUMENTS

WO    2005/033071    *    4/2005

OTHER PUBLICATIONS

Kaeding, W.W., et al., Selective Alkylation of Toluene to Produce para-Xylene, Journal of Catalysis, 1981, pp. 159-174, vol. 67.

(Continued)

*Primary Examiner*—Elizabeth D Wood
(74) *Attorney, Agent, or Firm*—Grady K. Bergen; Jim D. Wheelington; Griggs Bergen LLP

(57) ABSTRACT

A catalyst is formed from a phosphorus-containing ZSM-5-type zeolite. The ZSM-5-type zeolite has a silica/alumina molar ratio of at least 200. The phosphorus-containing ZSM-5-type zeolite also has a phosphorus content of at least 8% by weight of zeolite and has multiple phosphorus species exhibited by at least two $^{31}$P MAS NMR peaks with maxima at from about 0 to about −50 ppm. The catalyst may be used in aromatic alkylation by contacting the catalyst with a feed of an aromatic hydrocarbon and an alkylating agent under reaction conditions suitable for aromatic alkylation.

23 Claims, 6 Drawing Sheets

U.S. PATENT DOCUMENTS

| | | |
|---|---|---|
| 5,173,461 A | 12/1992 | Absil et al. |
| 5,178,748 A | 1/1993 | Casci et al. |
| 5,210,356 A | 5/1993 | Shamshoum et al. |
| 5,227,558 A | 7/1993 | Shamshoum et al. |
| 5,231,064 A | 7/1993 | Absil et al. |
| 5,233,102 A | 8/1993 | Butt et al. |
| 5,246,688 A | 9/1993 | Faust et al. |
| 5,248,841 A | 9/1993 | Young |
| 5,254,767 A | 10/1993 | Dwyer |
| 5,254,770 A | 10/1993 | Olson et al. |
| 5,294,332 A | 3/1994 | Klotz |
| 5,294,578 A | 3/1994 | Ho et al. |
| 5,315,033 A | 5/1994 | Butt et al. |
| 5,318,696 A | 6/1994 | Kowalski |
| 5,321,183 A | 6/1994 | Chang et al. |
| 5,336,478 A | 8/1994 | Dwyer et al. |
| 5,336,824 A | 8/1994 | Shamshoum et al. |
| 5,345,021 A | 9/1994 | Casci et al. |
| 5,348,643 A | 9/1994 | Absil et al. |
| 5,349,113 A | 9/1994 | Chang et al. |
| 5,365,003 A | 11/1994 | Chang et al. |
| 5,366,948 A | 11/1994 | Absil et al. |
| 5,367,100 A | 11/1994 | Gongwei et al. |
| 5,371,307 A | 12/1994 | Guth et al. |
| 5,378,670 A | 1/1995 | Kumar |
| 5,380,690 A | 1/1995 | Zhicheng et al. |
| 5,385,718 A | 1/1995 | Casci et al. |
| 5,387,732 A | 2/1995 | Shamshoum et al. |
| 5,399,336 A | 3/1995 | Guth et al. |
| 5,430,212 A | 7/1995 | Butt et al. |
| 5,430,213 A | 7/1995 | Hendriksen et al. |
| 5,446,234 A | 8/1995 | Casci et al. |
| 5,455,213 A | 10/1995 | Chang et al. |
| 5,456,821 A | 10/1995 | Absil et al. |
| 5,464,799 A | 11/1995 | Casci et al. |
| 5,475,179 A | 12/1995 | Chang et al. |
| 5,498,814 A | 3/1996 | Chang et al. |
| 5,503,818 A | 4/1996 | Nicolaides |
| 5,516,736 A | 5/1996 | Chang et al. |
| 5,523,510 A | 6/1996 | Pellet et al. |
| 5,534,239 A | 7/1996 | Fajula et al. |
| 5,536,894 A | 7/1996 | Degnan et al. |
| 5,541,146 A | 7/1996 | Chang et al. |
| 5,561,095 A | 10/1996 | Chen et al. |
| 5,563,310 A | 10/1996 | Chang et al. |
| 5,569,805 A | 10/1996 | Beck et al. |
| 5,571,768 A | 11/1996 | Chang et al. |
| 5,573,746 A | 11/1996 | Chen |
| 5,576,256 A | 11/1996 | Monque et al. |
| 5,607,888 A | 3/1997 | Chang et al. |
| 5,607,890 A | 3/1997 | Chen et al. |
| 5,646,314 A | 7/1997 | Crocco et al. |
| 5,648,580 A | 7/1997 | Chen et al. |
| 5,658,454 A | 8/1997 | Absil et al. |
| 5,675,047 A | 10/1997 | Beck et al. |
| 5,689,024 A | 11/1997 | Schmitt |
| 5,698,756 A | 12/1997 | Beck et al. |
| 5,780,563 A | 7/1998 | Chen et al. |
| 5,789,335 A | 8/1998 | Chen et al. |
| 5,811,613 A | 9/1998 | Bhat et al. |
| 5,833,840 A | 11/1998 | Absil et al. |
| 5,847,255 A | 12/1998 | Ghosh et al. |
| 5,902,919 A | 5/1999 | Chen et al. |
| 5,905,051 A | 5/1999 | Wu et al. |
| 5,907,073 A | 5/1999 | Ghosh |
| 5,922,922 A | 7/1999 | Harris et al. |
| 5,925,586 A | 7/1999 | Sun |
| 5,939,597 A | 8/1999 | Dessau et al. |
| 5,951,963 A | 9/1999 | He et al. |
| 5,952,535 A | 9/1999 | King et al. |
| 5,955,641 A | 9/1999 | Chen et al. |
| 5,990,031 A | 11/1999 | Ghosh |
| 5,994,603 A | 11/1999 | Mohr et al. |
| 6,034,283 A | 3/2000 | Ban et al. |
| 6,040,257 A | 3/2000 | Drake et al. |
| 6,046,128 A | 4/2000 | Kisen et al. |
| 6,047,544 A | 4/2000 | Yamamoto et al. |
| 6,048,816 A | 4/2000 | Brown et al. |
| 6,057,485 A | 5/2000 | Merrill et al. |
| 6,060,633 A | 5/2000 | Chen et al. |
| 6,074,975 A | 6/2000 | Yao et al. |
| 6,080,303 A | 6/2000 | Cao et al. |
| 6,080,698 A | 6/2000 | Zhang et al. |
| 6,083,865 A | 7/2000 | Drake et al. |
| 6,090,274 A | 7/2000 | Wu et al. |
| 6,090,991 A | 7/2000 | Butler et al. |
| 6,096,938 A | 8/2000 | Ghosh |
| 6,100,437 A | 8/2000 | Koehl et al. |
| 6,124,227 A | 9/2000 | Yao et al. |
| 6,150,293 A | 11/2000 | Verduijn et al. |
| 6,156,949 A | 12/2000 | Brown et al. |
| 6,160,191 A | 12/2000 | Smith et al. |
| 6,187,982 B1 | 2/2001 | Beck et al. |
| 6,211,104 B1 | 4/2001 | Shi et al. |
| 6,217,748 B1 | 4/2001 | Hatanaka et al. |
| 6,222,084 B1 | 4/2001 | Ghosh et al. |
| 6,251,263 B1 | 6/2001 | Hatanaka et al. |
| 6,268,305 B1 | 7/2001 | Butler et al. |
| 6,294,493 B1 | 9/2001 | Strohmaier et al. |
| 6,300,535 B1 | 10/2001 | van den Berge et al. |
| 6,306,790 B1 | 10/2001 | Rodriguez et al. |
| 6,342,153 B1 | 1/2002 | Guan et al. |
| 6,388,156 B1 | 5/2002 | Ou et al. |
| 6,395,664 B1 | 5/2002 | Boehner et al. |
| 6,399,530 B1 | 6/2002 | Chen et al. |
| 6,417,421 B1 | 7/2002 | Yao |
| 6,423,879 B1 | 7/2002 | Brown et al. |
| 6,444,610 B1 | 9/2002 | Yamamoto |
| 6,459,006 B1 | 10/2002 | Ou et al. |
| 6,469,095 B1 | 10/2002 | Gareiss et al. |
| 6,503,862 B1 | 1/2003 | Yamamoto |
| 6,504,072 B1 | 1/2003 | Brown et al. |
| 6,504,074 B2 | 1/2003 | Verduijn et al. |
| 6,506,954 B1 | 1/2003 | Brown et al. |
| 6,518,213 B1 | 2/2003 | Yamamoto et al. |
| 6,548,725 B2 | 4/2003 | Froment et al. |
| 6,566,293 B1 | 5/2003 | Vogt et al. |
| 6,589,901 B2 | 7/2003 | Yamamoto |
| 6,613,708 B1 | 9/2003 | Ou et al. |
| 6,613,951 B1 | 9/2003 | Brown et al. |
| 6,642,426 B1 | 11/2003 | Johnson et al. |
| 6,689,929 B2 | 2/2004 | Williams et al. |
| 6,699,811 B1 | 3/2004 | Mohr et al. |
| 6,723,297 B2 | 4/2004 | Chen et al. |
| 6,726,834 B2 | 4/2004 | Quesada et al. |
| 6,770,251 B2 | 8/2004 | Yoshikawa |
| 6,773,694 B1 | 8/2004 | Lesch et al. |
| 6,799,089 B2 | 9/2004 | Toulhoat |
| 6,811,684 B2 | 11/2004 | Mohr et al. |
| 6,812,181 B2 | 11/2004 | van der Berge et al. |
| 6,864,399 B2 | 3/2005 | Merrill et al. |
| 7,285,511 B2 * | 10/2007 | Ghosh et al. ............ 502/64 |
| 2003/0004383 A1 | 1/2003 | Brown et al. |
| 2005/0070749 A1 | 3/2005 | Ghosh et al. |
| 2005/0209492 A1* | 9/2005 | Ghosh et al. ............ 585/467 |

OTHER PUBLICATIONS

Hibino, T., et al., Shape-Selectivity Over HZSM-5 Modified by Chemical Vapor Deposition of Silicon Alkoxide, Journal of Catalysis 128, 1991, pp. 551-558.

Wang, I., et al., Para-selectivity of Diaklybenzenes over Modified HZSM-5 by Vapour Phase Deposition of Silica, Applied Catalysis, 54, 1989, 257-266.

Das, J., et al., Ethylbenzene Dealkylation and Realkylation over Pore Size Regulated MFI Zeolite, Ind. Eng. Chem. Res., 32, 1993, pp. 2525-2529.

Yashima, T., et al., Selective Formation of p-Xylene by Alkylation of Toluene with Methanol on ZSM-5 Type Zeolites, Stud. Surf. Sci. Catal., 1981, 7, pp. 739-751.

Sayed, M. B., et al., The Effect of Modification with Boron on the Catalytic Activity and Selectivity of HZSM-5, Journal of Catalysis 101, 1986, pp. 43-55.

Kim, J.-H., et al., Para-selectivity of Metallosilicates with MFI Zeolite Structure Zeolites, vol. 11, 1991, pp. 59-63.

Kim, J.-H., et al., Preparation of Highly Para-selective Metallosilicate Catalysts for Alkylation of Ethylbenzene with Ethanol, Applied Catalysis A:100, 1993, pp, 27-36.

Kim, J.-H, et al., Generation of Shape-Selectivity of p-Xylene Formation in the Synthesized ZSM-5 Zeolites, Journal of Catalysis 173, 1998, pp. 433-439.

Sayed, M. B., et al., The Effect of Boron on ZSM-5 Zeolite Shape Selectivity and Activity, Journal of Catalysis 116, 1989, pp. 1-10.

* cited by examiner

METHOD OF MAKING A PHOSPHORUS-MODIFIED ZEOLITE CATALYST

This application is a continuation of U.S. patent application Ser. No. 11/136,877, filed May 25, 2005, now U.S. Pat. No. 7,399,727, which is a continuation-in-part of U.S. patent application Ser. No. 10/831,729, filed Apr. 23, 2004, now U.S. Pat. No. 7,285,511, each of which is herein incorporated by reference in its entirety.

TECHNICAL FIELD

The invention relates generally to the alkylation of aromatic compounds and catalysts used for such reactions.

BACKGROUND

Para-xylene is a valuable substituted aromatic compound due to its great demand for production of terephthalic acid, a major component in forming polyester fibers and resins. It can be commercially produced from hydrotreating of naphtha (catalytic reforming), steam cracking of naphtha or gas oil, and toluene disproportionation.

Alkylation of toluene with methanol, which is also known as toluene methylation, has been used in laboratory studies to produce para-xylene. Toluene methylation has been known to occur over acidic catalyst, particularly over zeolite or zeolite-type catalyst. In particular, ZSM-5-type zeolite, zeolite Beta and silicaaluminophosphate (SAPO) catalysts have been used for this process. Generally, a thermodynamic equilibrium mixture of ortho (o)-, meta (m)- and para (p)-xylenes can be formed from the methylation of toluene, as is illustrated by the reaction below.

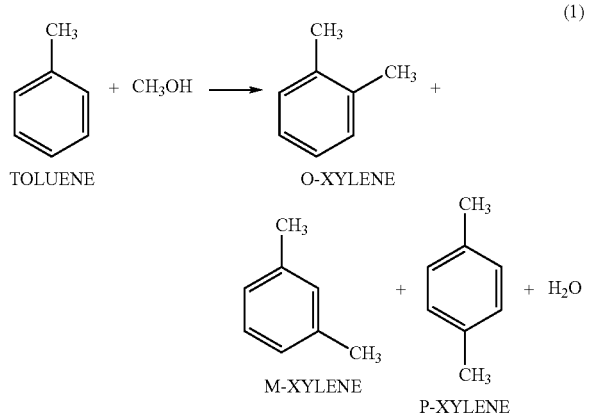

Thermodynamic equilibrium compositions of o-, m-, and p-xylenes may be around 25, 50 and 25 mole %, respectively, at a reaction temperature of about 500° C. Such toluene methylation may occur over a wide range of temperatures, however. Para-xylene can be separated from mixed xylenes by a cycle of adsorption and isomerization. Byproducts such as C9+ and other aromatic products can be produced by secondary alkylation of the xylene product.

A significantly higher amount of p-xylene can be obtained in toluene methylation reaction if the catalyst has shape selective properties. Shape selective properties can be obtained in modified zeolite catalysts by modifying zeolite pore opening size, inactivation of the external surface of the zeolite or controlling zeolite acidity. Toluene methylation may occur over modified ZSM-5 or ZSM-5-type zeolite catalyst giving xylene products containing significantly greater amounts of p-xylene than the thermodynamic concentration.

Phosphoric acid and other phosphorus-containing compounds have been used to modify ZSM-5 zeolite catalysts to provide shape selective properties. U.S. Pat. No. 6,504,072, for instance, discloses the treatment of ZSM-5 zeolite catalyst with phosphorus (P) to control the reduction of diffusivity and pore volume prior to severe steaming to provide a para-selective catalyst. U.S. Pat. No. 4,554,394 discusses the treatment of ZSM-5 zeolites with a vapor phase organophosphorus reagent to provide para-selective properties. Although such phosphorus-treated ZSM-5 catalysts may have a high selectivity for p-xylene, they tend to deactivate at a very fast rate. For example, the catalyst may lose greater than 50% of its initial activity within a day. This may possibly be due to coke deposition on the catalyst.

Because there are a number of technical hurdles for toluene methylation to be commercially successful, improvements are needed.

BRIEF DESCRIPTION OF THE DRAWINGS

For a more complete understanding of the present invention, reference is now made to the following descriptions taken in conjunction with the accompanying figures, in which.

DETAILED DESCRIPTION

Figure 1:
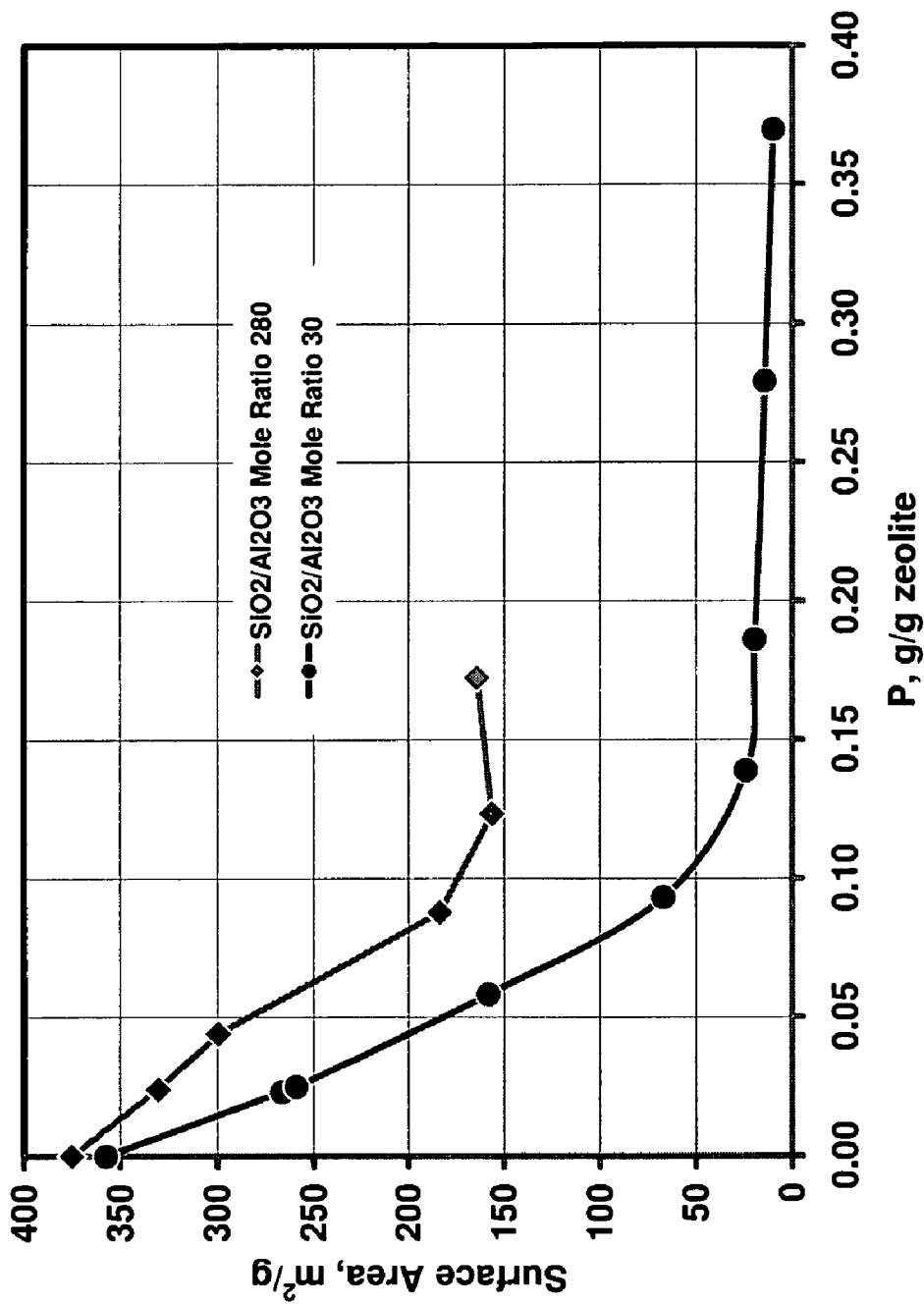
FIG. 1 is a plot of BET surface area of different $H_3PO_4$-modified ZSM-5 zeolite catalysts as a function of the amount of phosphorus used in the modifications.

As used herein, the expression "ZSM-5-type" is meant to refer to those zeolites that are isostructurally the same as ZSM-5 zeolites. Additionally, the expressions "ZSM-5" and "ZSM-5-type" may be used herein interchangeably to encompass one another and should not be construed in any limiting sense. The ZSM-5 zeolite catalysts and their preparation are described in U.S. Pat. No. 3,702,886, which is herein incorporated by reference.

As used herein, catalytic activity can be expressed as the % moles of toluene converted with respect to the moles of toluene fed and can be defined as:

$$\text{Mole \% Toluene Conversion} = [(T_i - T_o)/T_i] \times 100 \quad (2)$$

where, $T_i$ is the number of moles of toluene fed and $T_o$ is the number of moles toluene unreacted. As used herein, selectivity for mixed-xylenes may be expressed as:

$$\text{Mole \% Mixed Xylene Selectivity} = [X_{mx}/(T_i - T_o)] \times 100 \quad (3)$$

where, $X_{mx}$ is the number of moles of total (o-, m- or p-) xylenes in the product. As used herein, selectivity for p-xylene may be expressed as:

$$\text{Mole \% p-Xylene Selectivity} = (X_p/X_{mx}) \times 100 \quad (4)$$

where, $X_p$ is the number of moles of p-xylene.

Modification of ZSM-5 zeolite with phosphorus containing compound(s) and heat treatment may cause the formation of certain phosphorus-species within the zeolite pores and channels, which may result in the reduction of surface area and pore volume. Such modified catalysts may provide increased para-selectivity without the need for subsequent steaming at a high temperature (e.g., 700° C. or higher) or additional treatment of the catalyst. The phosphorus-modified ZSM-5 catalysts provide increased activity and selectivity for aromatic alkylation. In certain instances, increased catalyst activity and total xylenes selectivity may be achieved during use in toluene methylation for particular ZSM-5 zeolite catalysts, while still providing high p-xylene selectivity.

In the present invention, ZSM-5 zeolite is modified with a P-containing compound and heat treated to provide shape selectivity. The starting ZSM-5 zeolite may be an $NH_4$- or H-form zeolite, which may be in the form of a powder or any other form. In the present invention, the ZSM-5 zeolite catalyst may include those having a silica/alumina molar ratio of greater than 25 prior to modification with a phosphorus containing compound. As is discussed below, the silica/alumina ratio of the initial ZSM-5 zeolite catalyst may have an effect on catalyst activity and xylene selectivity of the subsequently treated catalyst in toluene methylation. In certain instances, the $SiO_2/Al_2O_3$ mole ratio of starting ZSM-5 may be from 200, 280, 300 to 1000 or more to achieve higher activity with increased p-xylene selectivity.

The phosphorus compound may be a phosphorus-containing acid, such as phosphoric acid ($H_3PO_4$) and phosphorus acid ($H_3PO_3$). For phosphorus-containing acids, the acid may be used at a concentration of greater than 50 wt %, with from 50 wt % to about 85 wt % being suitable. The phosphorus compound may also include other non-acid phosphorus-containing compounds, such as ammonium hydrogen phosphate (($NH_4)_2HPO_4$). The amount of phosphorus used may provide a phosphorus content of the treated catalyst of from 0.04 g P/g zeolite or more. In certain applications, phosphorus may be incorporated into the catalyst in amounts of from 0.08 g P/g zeolite or more, more specifically from about 0.09 g P/g zeolite to about 0.10 g P/g zeolite or to about 0.15 g P/g zeolite.

The phosphorus treatment may be carried out by various techniques. This may include slurry evaporation and wet incipient methods. In slurry evaporation, the phosphorus may be incorporated into the catalyst by preparing a slurry of the zeolite and an aqueous solution of the phosphorus compound. Heating of the slurry may be used to facilitate treatment of the zeolite catalyst and to evaporate liquids. Heating of the slurry to temperatures of from about 25° C. or more, with from 70° C. to about 100° C. being suitable in most instances. The slurry may also be stirred or agitated during this step to ensure uniform treatment. The evaporation of the liquid from the zeolite slurry can be alternatively achieved by spray-dry technique which is well known in the art.

In the wet incipient method, an aqueous solution of the phosphorus compound is added, such as by spraying, to dry zeolite without forming a slurry. The dry zeolite, which may be initially in the form of a powder, may be mixed with the phosphorus compound to form a dough. If necessary, water may be added to the mixture to facilitate formation of the zeolite dough. The dough may then be heated at similar temperatures to those of the slurry technique to facilitate evaporation of water.

The P-treated zeolite may be calcined at 250° C. or more, more particularly, a temperature between 300° C. and 600° C., more particularly from about 400° C. to about 570° C., in an environment containing oxygen, typically air. Calcining may take place over time, typically from several minutes to one hour or more. Calcining may also take place by gradually increasing the temperature over time.

The phosphorus-modified zeolite catalyst may be used unbound or be bound with a binder. Examples of suitable binders include such materials as alumina, clay, and silica. Those techniques used for preparing the bound catalyst are well known in the art.

The treated ZSM-5 zeolite catalyst may provide a total pore volume of from about 0.2 ml/g or less. More particularly, the total pore volume may range from about 0.18 ml/g to about 0.07 ml/g. The BET surface area of the ZSM-5 zeolite catalyst may range from less than 300 $m^2/g$ to about 10 $m^2/g$.

The phosphorus-modified catalyst contains an insignificant amount of tetrahedral/structural Al in the zeolite framework showing a weak $^{27}$Al-MAS NMR peak at around 50 ppm, but the catalyst may contain "debris" or extra framework aluminum (EFAl) inside zeolite pores showing a strong $^{27}$Al-MAS NMR peak at about −14 ppm. The ratio of framework aluminum over extra-framework aluminum for the treated zeolite catalyst may range from about 0.12 to 0.25.

The phosphorus modified zeolite contains different P-species showing $^{31}$P-MAS NMR peak(s) having maxima at from about 0 ppm to about −50 ppm. The P-species may be free phosphate, or bonded to extra-framework Al, or AlPO/SAPO, or polyphosphate type species.

The treated catalyst may be used as a non-steamed catalyst in toluene methylation. The phosphorus-treated ZSM-5 zeolite catalyst may also be steamed at low or mild temperatures. The steaming may occur by contacting the catalyst with steam in the presence of hydrogen gas or other inert gases. Steaming temperatures may range from about 150° C. to about 250° C., 300° C. or 350° C. This may be accomplished separately or in situ within the reactor, prior to any aromatic alkylation reaction or introduction of any reaction feed. Steaming may be conducted from a few minutes to several hours. The use of catalyst steaming at mild temperatures is described in the co-pending U.S. patent application Ser. No. 11/122,919, filed May 5, 2005, entitled "Hydrothermal Treatment of Phosphorus-Modified Zeolite Catalysts," which is herein incorporated by reference.

The modified catalyst may be contacted with an appropriate feed of an aromatic hydrocarbon and an alkylating agent under alkylation reaction conditions to carry out aromatic alkylation. The catalyst has particular application for use in toluene methylation utilizing a toluene/methanol feed. A gas cofeed may also be optionally used. The cofeed gas may include hydrogen or an inert gas. The cofeed gas may be used in an amount of at least 0.1 mole per mole of aromatic alkylation feed. As used herein, the expression "alklyation feed" is meant to encompass the aromatic compound and the alkylating agent. As used herein, the expression "methylation feed" is meant to encompass the feed of toluene and methanol.

In addition to cofeed gas, water or steam may also be introduced into the reactor as cofeed along with the alkylation feed. The water or steam used for the methylation reaction may be introduced with or without hydrogen or inert gas as cofeed with the alkylation feed to the reactor during the start up of the alkylation reaction or it may be introduced subsequent to initial start up. In either case, liquid water may be added and vaporized prior to its mixing with cofeed gas (if any) and alkylation feed.

The reactor pressure for toluene methylation or other aromatic alkylation may vary, but typically ranges from about 10 to about 1000 psig. Reactor temperatures may typically range from 400 to 700° C.

The reaction may be carried in a variety of different reactors that are commonly used for carrying out aromatic alkylation reactions. Single or multi reactors in series and/or parallel are suitable for carrying out the toluene methylation.

The modified catalyst is useful in toluene methylation for preparing a xylene product from a feed of toluene and methanol that has increased selectivity for p-xylene. In particular, the catalyst may provide greater than 80%, 85% and 90% para-xylene selectivity when used in toluene methylation. Additionally, in certain instances, greater than 90% of total xylene selectivity may be achieved.

The following examples serve to further illustrate the invention.

EXAMPLES

Catalyst Preparation

Catalyst A-I

The starting material was an $NH_4$-ZSM-5 zeolite powder having a $SiO_2/Al_2O_3$ mole ratio of 30. An aqueous slurry containing 11.63 g of $NH_4$-ZSM-5 zeolite and 50 ml of deionized water was prepared in a 400 ml beaker. The beaker was placed on a hot plate and the zeolite suspension was stirred using a magnetic stir bar. The temperature of the suspension was maintained around 90° C. 1.08 g of phosphoric acid (85 wt % in aqueous) was added drop wise into the beaker. Heating was continued until all liquid was evaporated. The phosphoric-acid modified zeolite was dried at 90° C. to 120° C. for at least four hours and at 340° C. to 360° C. for three hours and then calcined at 510° C. to 530° C. under air for 10 hours. The calcined zeolite was then crushed and sized using 20 and 40 mesh screens. A series of catalysts A-H (see Table 1) were prepared by varying the amount of phosphoric acid with respect to the amount of starting $NH_4$-ZSM-5 powder. A non-phosphorus ZSM-5 (Catalyst I) was also prepared by calcining (using the same temperature profile described above) the $NH_4$-ZSM-5 zeolite powder having a $SiO_2/Al_2O_3$ mole ratio of 30. BET surface area (SA) and total pore volume (PV) (measured by $N_2$ adsorption) for Catalysts A-I are shown in Table 1 and in FIGS. 1 and 2.

TABLE 1

| Catalyst | Water, ml | Zeolite Powder, g | $H_3PO_4$ Content, g[a] | P, g/g zeolite[a] | SA, m2/g | PV, ml/g |
|---|---|---|---|---|---|---|
| A | 100 | 46.50 | 4.00 | 0.023 | 266.4 | 0.483 |
| B | 50 | 11.63 | 1.08 | 0.025 | 259.0 | 0.340 |
| C | 50 | 11.63 | 2.52 | 0.058 | 157.8 | 0.212 |
| D | 50 | 11.64 | 4.04 | 0.093 | 66.9 | 0.189 |

TABLE 1-continued

| Catalyst | Water, ml | Zeolite Powder, g | $H_3PO_4$ Content, g[a] | P, g/g zeolite[a] | SA, m2/g | PV, ml/g |
|---|---|---|---|---|---|---|
| E | 50 | 11.63 | 6.01 | 0.139 | 24.0 | 0.183 |
| F | 50 | 11.63 | 8.05 | 0.186 | 18.6 | 0.179 |
| G | 50 | 11.64 | 12.51 | 0.279 | 14.2 | 0.077 |
| H | 50 | 11.64 | 16.01 | 0.370 | 9.7 | 0.079 |
| I | — | — | 0 | 0 | 357.2 | 0.579 |

Figure 2:
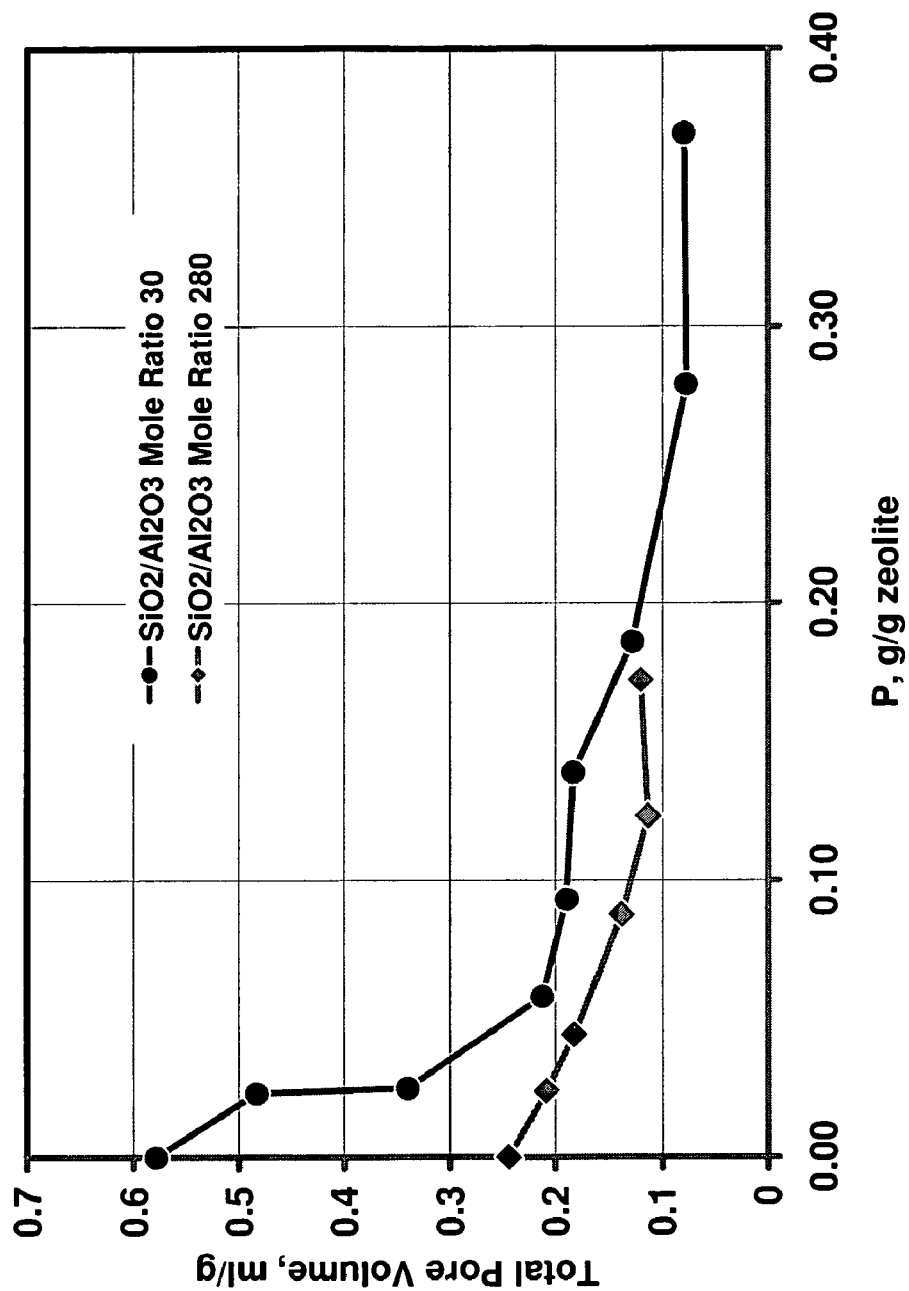
FIG. 2 is a plot of total pore volume of different $H_3PO_4$-modified ZSM-5 zeolite catalysts as a function of the amount of phosphorus used in the modification.

[a]Total amount of phosphoric acid (85% in aqueous) or P used in the preparation As can be seen from Table 1 and FIGS. 1 and 2, a sharp decrease in BET surface area (SA) and total pore volume (PV) of the zeolite Catalysts A-H prepared by using starting $NH_4$-ZSM-5 having $SiO_2/Al_2O_3$ mole ratio of 30 with increasing amounts of phosphoric acid or phosphorus was observed.

Catalyst J-O

The starting material was an $NH_4$-ZSM-5 zeolite powder having a $SiO_2/Al_2O_3$ mole ratio of 280. A slurry containing 12.09 g of $NH_4$-ZSM-5 zeolite and 50 ml of deionized water was prepared in a 400 ml beaker. The beaker was placed on a hot plate and the zeolite suspension was stirred using a magnetic stir bar. The temperature of the suspension was maintained around 90° C. 1.08 g phosphoric acid (85 wt % in aqueous) was added drop wise into the beaker. Heating was continued until all liquid was evaporated. The phosphoric-acid modified zeolite was dried at 90° C. to 120° C. for at least four hours and at 340° C. to 360° C. for three hours and then calcined at 510° C. to 530° C. under air for 10 hours. The calcined zeolite was then crushed and sized using 20 and 40 mesh screens. A series of Catalysts J-N (see Table 2) were prepared by varying the amount of phosphoric acid with respect to the amount of starting $NH_4$-ZSM-5 powder. A non-phosphorus ZSM-5 (Catalyst O) was also prepared by calcining (using the same temperature profile described above) the $NH_4$-ZSM-5 zeolite powder having a $SiO_2/Al_2O_3$ mole ratio of 280. BET surface area and total pore volume (measured by $N_2$ adsorption) for catalysts J-O are shown in Table 2 and FIGS. 1 and 2. The decrease in BET surface area (SA) and total pore volume (PV) for catalyst made using starting $NH_4$-ZSM-5 having $SiO_2/Al_2O_3$ mole ratio 280 is not as prominent compared to that for catalysts A-J prepared by using starting $NH_4$-ZSM-5 having $SiO_2/Al_2O_3$ mole ratio 30.

TABLE 2

| Catalyst | Water, ml | Zeolite Powder, g | $H_3PO_4$ Content, g[a] | P, g/g zeolite[a] | SA, m2/g | PV, ml/g |
|---|---|---|---|---|---|---|
| J | 50 | 12.09 | 1.08 | 0.024 | 330.7 | 0.208 |
| K | 50 | 24.09 | 3.95 | 0.044 | 299.4 | 0.182 |
| L | 100 | 48.38 | 15.8 | 0.088 | 183.2 | 0.138 |
| M | 100 | 48.39 | 23.7 | 0.123 | 156.2 | 0.113 |
| N | 50 | 12.09 | 7.75 | 0.172 | 163.7 | 0.120 |
| O | — | — | 0 | 0 | 375.0 | 0.244 |

[a]Total amount of phosphoric acid (85% in aqueous) or P used in the preparation.

Catalyst P-S

The starting material was an $NH_4$-ZSM-5 zeolite powder having a $SiO_2/Al_2O_3$ mole ratio of 280. A slurry containing 51.66 g of $NH_4$-ZSM-5 zeolite and 200 ml of deionized water was prepared in a 400 ml beaker. The beaker was placed on a hot plate and the zeolite suspension was stirred using a magnetic stir bar. The temperature of the suspension was maintained around 90° C. 9.07 g ammonium hydrogen phosphate, (NH$_4$)$_2$HPO$_4$, was dissolved in 50 ml water and the salt solution was added drop wise into the beaker. Heating was continued until all liquid was evaporated. The ammonium hydrogen phosphate modified zeolite was dried at 90° C. to 120° C. for at least four hours and at 340° C. to 360° C. for three hours and then calcined at 510° C. to 530° C. under air for 10 hours. The calcined zeolite was then crushed and sized using 20 and 40 mesh screens. A series of Catalysts P-S (see Table 3) were prepared by varying the amount of ammonium hydrogen phosphate with respect to the amount of starting NH$_4$-ZSM-5 powder. BET surface area (SA) and total pore volume (PV) (measured by N$_2$ adsorption) for Catalysts P-S are shown in Table 3.

TABLE 3

| Catalyst# | Water, ml | Zeolite Powder, g | (NH4)2HPO$_4$, g[a] | P, g/g zeolite[a] | SA, m2/g | PV, ml/g |
|---|---|---|---|---|---|---|
| P | 200 | 30.09 | 2.49 | 0.018 | 317.2 | 0.208 |
| Q | 200 | 51.66 | 9.07 | 0.039 | 278.3 | 0.179 |
| R | 200 | 51.66 | 12.85 | 0.055 | 241.0 | 0.155 |
| S | 200 | 48.38 | 18.14 | 0.082 | 216.2 | 0.131 |

[a]Total amount of ammonium hydrogen phosphate or P used in the preparation

There was little or no difference in surface area and pore volume between the catalyst series J-N made by using phosphoric acid and catalyst series P-S made by using ammonium hydrogen phosphate at a given amount of phosphorus. Thus the use of phosphoric acid or ammonium hydrogen phosphate as a phosphorus-containing compound for preparing p-xylene selective catalysts may not make a significant difference.

Catalyst T-W

The starting material was an NH$_4$-ZSM-5 zeolite powder having a SiO$_2$/Al$_2$O$_3$ mole ratio of 280. A slurry containing 400.0 g of NH$_4$-ZSM-5 zeolite and 800 ml of deionized water was prepared in a 2 L beaker. The beaker was placed on a hot plate and the zeolite suspension was stirred using a mechanical stirrer. The temperature of the suspension was maintained above 90° C. 182.5 g phosphoric acid (85 wt % in aqueous) was added drop wise into the beaker. Heating was continued until all liquid was evaporated. The phosphoric-acid modified zeolite was divided into four samples and each sample was dried or calcined at different maximum temperatures: Catalyst T (dried at 60° C.), Catalyst U (dried at 250° C.), Catalyst V (calcined at 350° C.) and Catalyst W (calcined at 510° C.).

Solid State $^{27}$Al MAS-NMR

Solid state Magic Angle Spinning (MAS) NMR spectra were recorded on the ZSM-5 zeolites with 400 MHz spectrometer ($^{27}$Al at 104.5 MHz) at room temperature. Samples were packed in silicon nitride rotors (Si$_3$N$_4$) and spun at 13 to KHz sample spinning (about 800000 rpm). A 10 degree tip and recycle delay of 0.5 s were used to avoid saturation. About 4000 to 10000 scans were accumulated to signal average and to improve signal/noise ratio. Proton decoupling was not employed. All spectra were referenced to aluminum chloride hexahydrate (run separately in a tube) at 0.0 ppm on the chemical shift scale. This leads to an internal reference of 104.85 ppm on the aluminum nitride (small impurity in the silicon nitride rotors) peak.

Figure 3:
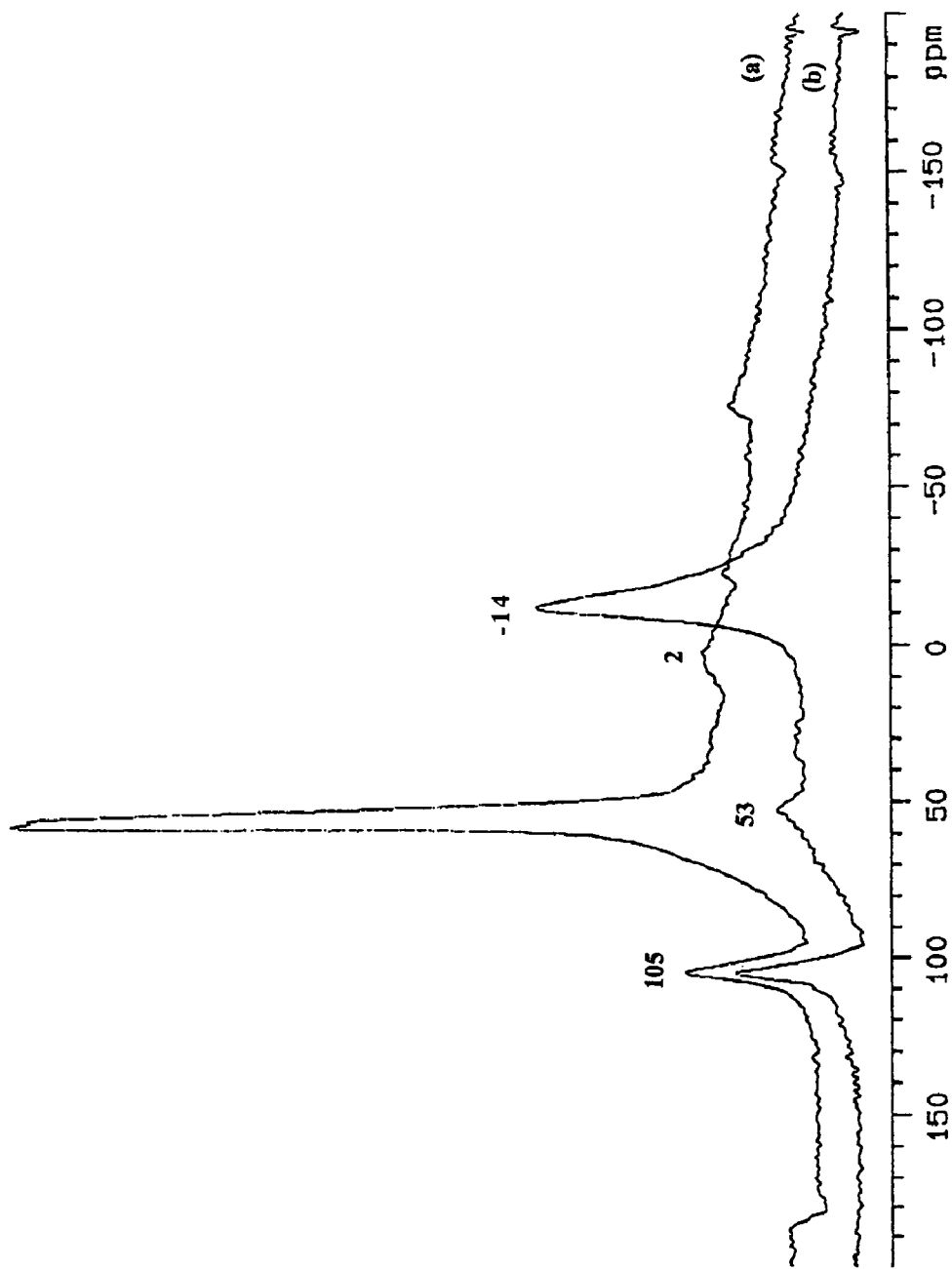
FIG. 3 shows $^{27}Al$ MAS-NMR spectra of (a) $NH_4$-ZSM-5 zeolite having $SiO_2/Al_2O_3$ mole ratio 280, and of (b) phosphorus-modified ZSM-5 zeolite catalyst.

$^{27}$Al MAS-NMR spectra were recorded on the starting NH$_4$-ZSM-5 zeolite having SiO$_2$/Al$_2$O$_3$ mole ratio 280 and the phosphorus modified zeolites. The starting NH$_4$-ZSM-5 zeolite sample showed a strong $^{27}$Al MAS-NMR peak at around 55 ppm attributing to framework tetrahedral (4 coordinated) aluminum (spectrum a, FIG. 3). The sharpness of the resonance and the symmetry indicate the zeolite is relatively crystalline with very few lattice defects. The framework Al is responsible for zeolite acidity and the starting zeolite sample showed strong acidity. The P-modified sample shows a weak peak at about 55-50 ppm region assigned to structural tetrahedral aluminum (spectrum b, FIG. 3). The tetrahedral aluminum peak is severely distorted, indicating presence of nested silanols caused by holes in the structure upon removal of some of the framework aluminum. The adjacent peak (30-40 ppm) peak is due to severely distorted but still in the framework aluminum atoms probably either in the 3 or 5 coordination with oxygens. The tallest peak in spectrum a at −14 ppm is from octahedrally coordinated aluminum atoms that are formed when tetrahedrally coordinated framework aluminum is removed from the zeolite framework by the phosphate modification process as mentioned above.

$^{31}$P MAS NMR

MAS NMR spectra were recorded on the P/ZSM-5 zeolite with 400 MHz spectrometer ($^{31}$P at 161.7 MHz) at room temperature. Samples were packed in silicon nitride rotors (Si$_3$N$_4$) and spun at 13 to KHz sample spinning (about 800000 rpm). A 30 degree tip and a recycle delay of 15 s were used to avoid saturation. About 4000 to 10000 scans were accumulated to signal average and improve signal/noise ratio. Proton decoupling was not employed. All spectra were doubly referenced to tetramethyl diphosphine disulphide at 37.8 ppm and 85% phosphoric acid (run separately in a tube) at 0.0 ppm on the chemical shift scale.

Figure 4:
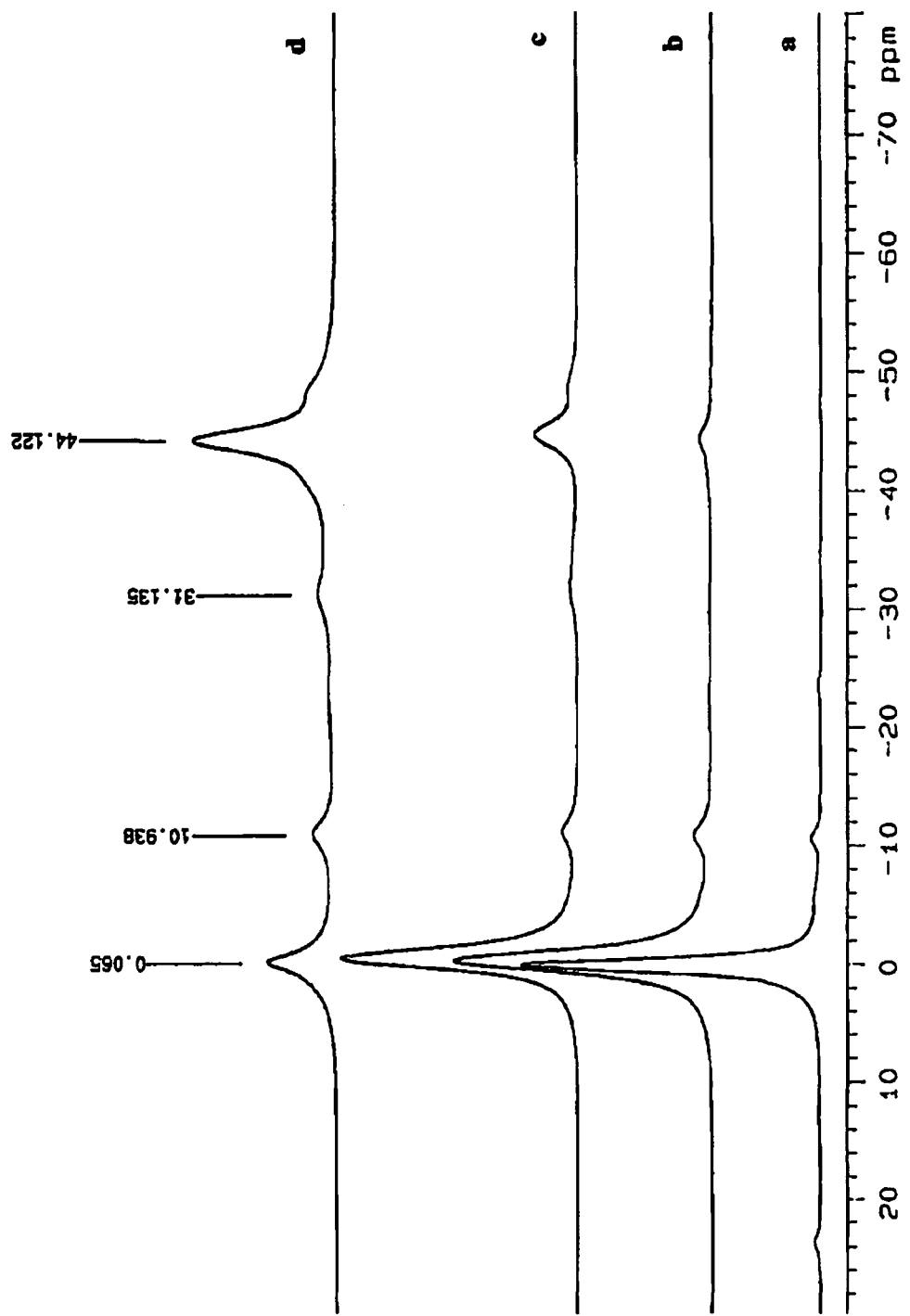
FIG. 4 shows $^{31}P$ MAS-NMR spectra of phosphorus-modified catalysts after drying/calcining at different temperatures: (a) dried at 60° C. (Catalyst T), (b) dried at 250° C. (Catalyst U), (c) dried at 350° C. (Catalyst V), and (d) calcined at 510° C. (Catalyst W)

$^{31}$P MAS-NMR spectra were recorded on the P-treated ZSM-5 (SiO$_2$/Al$_2$O$_3$ mole ratio 280) after drying or calcining at different temperatures. A strong peak at around 0 ppm and a weak peak at around −11 ppm were observed for P/ZSM-5 after drying at 60° C. (catalyst T, FIG. 4, spectrum a). The peak at about 0 ppm may be assigned to free phosphate occluded in zeolite pores/channels. As the drying or calcining temperature was increased the peak at about 0 ppm decreased with the appearance of new peaks of from about −20 ppm to about −50 ppm (catalyst U-W, FIG. 4, spectra b-d). The weak peak observed at about −11 ppm remained almost unchanged with the change of drying/calcining temperature. The peaks at about −11, about −31 and about −44 ppm were assigned to phosphorus bound to various phosphorus species such as extra-framework Al, AlPO/SAPO and polyphosphate. Apparently, the state of phosphorus in the zeolite changed during drying/calcinations.

X-Ray Diffraction Pattern (XRD)

The X-ray diffraction patterns (XRD) of NH$_4$-ZSM-5 and P-treated catalysts (U-W) were recorded on a Philips (X'Pert model) diffractometer over a range of 5-55° at a scan rate 2° per minute using CuKα1 radiation. The peak intensities of the ZSM-5 decreased after the P-treatment of NH$_4$-ZSM-5 zeolite. Apparently, the P-treatment caused some damage to the initial zeolite structure. The P-treated ZSM-5 catalyst started to show new peaks at d-spacing 8.02, 6.53 and 3.52 Å after catalyst dried at 250° C.; the intensities of the new peaks increased further when the catalyst was dried/calcined at 350° C. and 510° C. The X-ray diffraction peaks are set forth in Table 4 below.

TABLE 4

| Powder XRD Intensity* | |
|---|---|
| d-spacing [Å] | Intensity |
| 11.09 | 100 |
| 10.00 | 55 |

TABLE 4-continued

Powder XRD Intensity*

| d-spacing [Å] | Intensity |
|---|---|
| 9.88 | 42 |
| 9.68 | 17 |
| 8.02 | 8 |
| 6.68 | 7 |
| 6.53 | 8 |
| 6.33 | 8 |
| 5.98 | 16 |

TABLE 4-continued

Powder XRD Intensity*

| d-spacing [Å] | Intensity |
|---|---|
| 5.69 | 7 |
| 5.56 | 9 |
| 4.25 | 9 |
| 4.00 | 6 |
| 3.84 | 50 |
| 3.81 | 31 |
| 3.71 | 27 |
| 3.64 | 10 |
| 3.52 | 22 |
| 2.98 | 8 |
| 2.78 | 5 |

*Intensities shown are scaled in arbitrary units so that most intense peak is 100.

Examples 1-19

Figure 5:
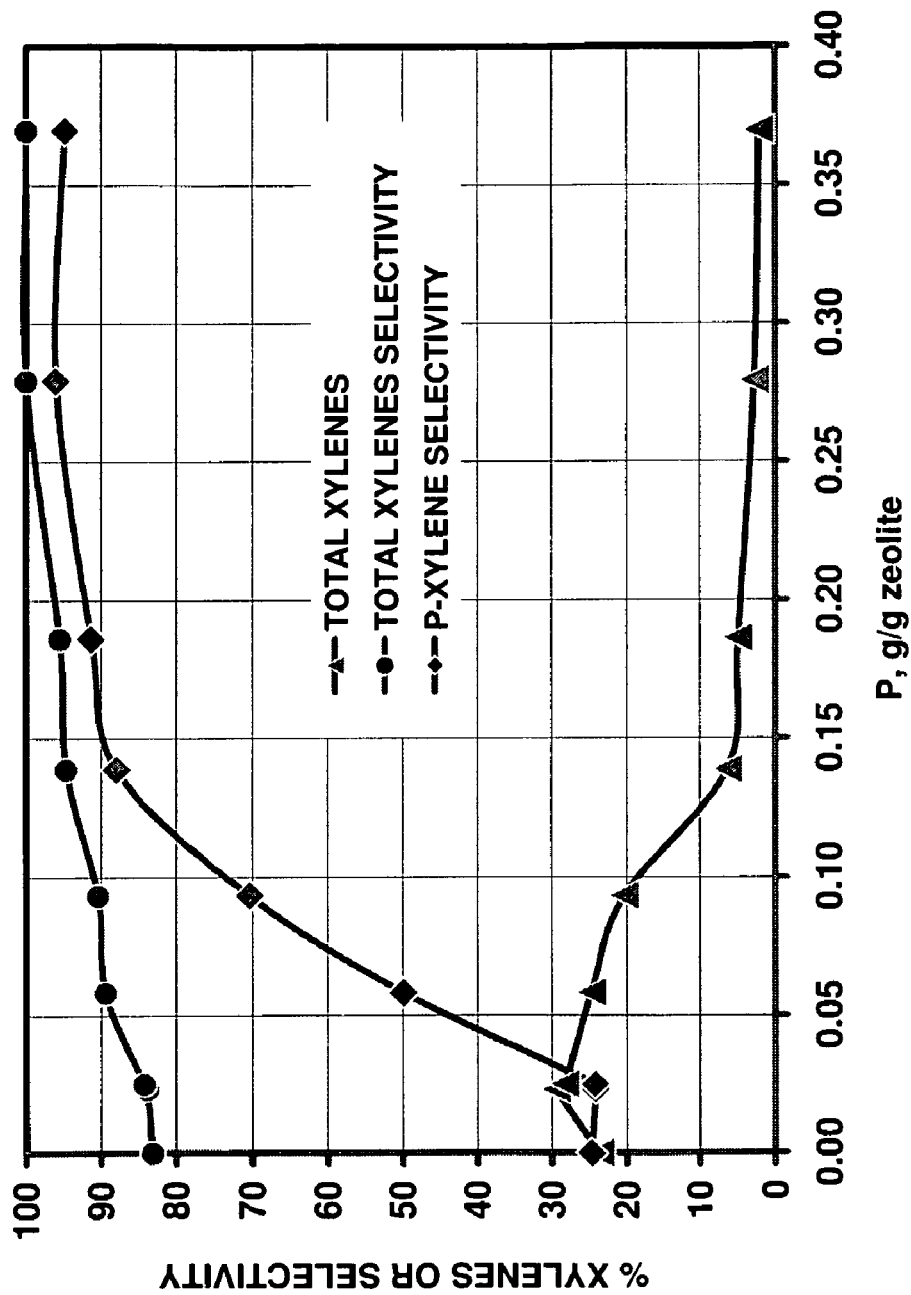
FIG. 5 is a plot of wt % total xylenes and selectivity to total xylenes and p-xylene for a liquid product stream obtained from toluene methylation over $H_3PO_4$ modified ZSM-5 zeolite catalysts having a starting $SiO_2/Al_2O_3$ mole ratio of 30 as a function of amount of phosphorus used in the modification.
Figure 6:
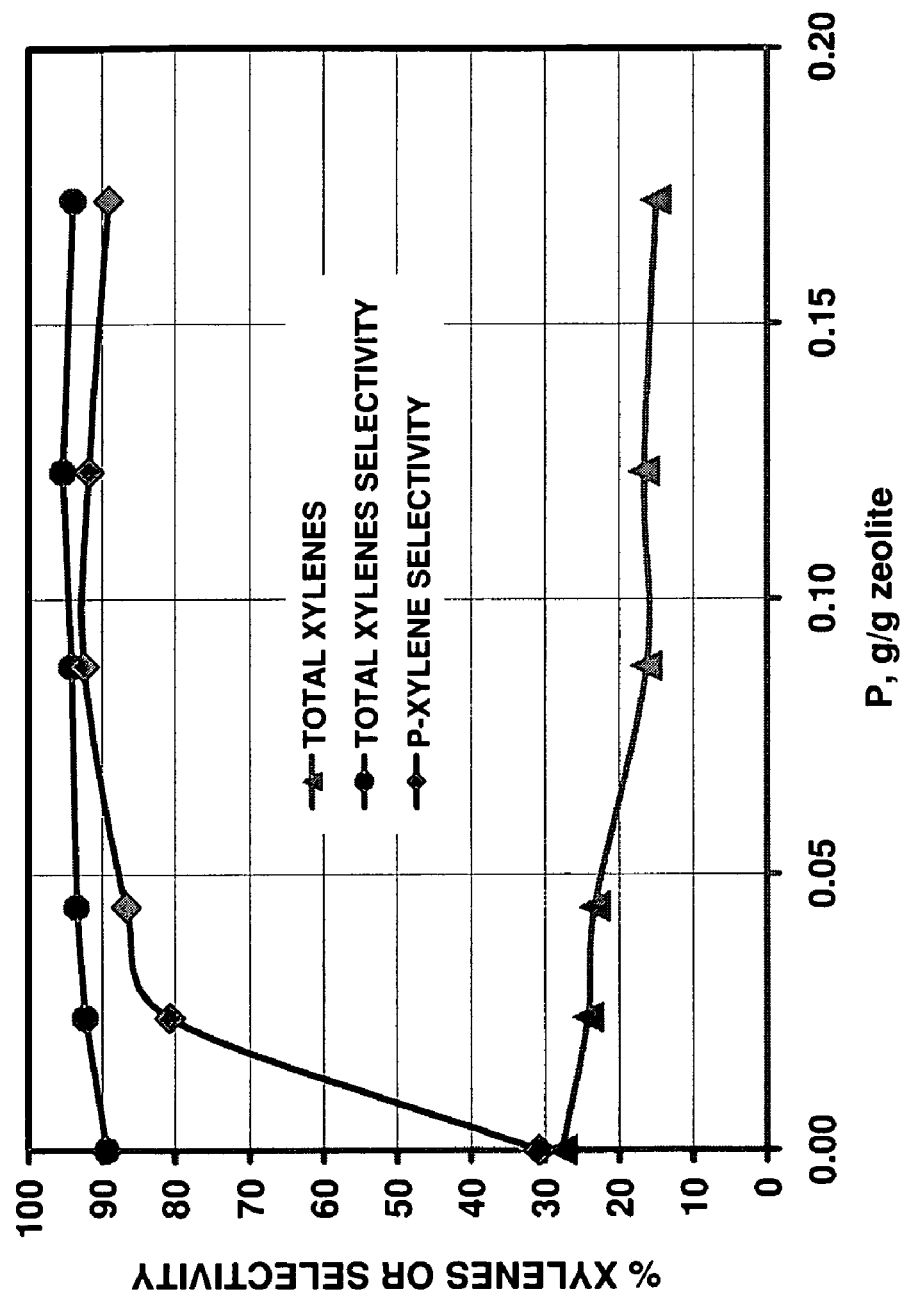
FIG. 6 is a plot of wt % total xylenes and selectivity to total xylenes and p-xylene for a liquid product stream obtained from toluene methylation over $H_3PO_4$ modified ZSM-5 zeolite catalysts having a starting $SiO_2/Al_2O_3$ mole ratio of 280 as a function of amount of phosphorus used in the modification.

The catalysts A-I, J-O and P-S described above and in Tables 1-3, were used in toluene methylation reactions. The reactions were each carried out in a fixed bed, continuous flow type reactor. In each case, a catalyst was dried by slowly raising the catalyst bed temperature (about 5° C./min) to 200° C. under hydrogen ($H_2$) flow for at least one hour. A premixed methylation feed of toluene and methanol (molar ratio 2/1) was added to the reactor at 200° C. and the catalyst bed inlet temperature was increased to about 500° C. The liquid hourly space velocity (LHSV) (based on methylation feed) was maintained at about 31 $hr^{-1}$ and a cofeed of $H_2$ gas was fed and maintained to provide a $H_2$/(toluene+methanol) molar ratio of about 0.1. Water was added to the methylation feed and was vaporized prior to introduction to reactor. The $H_2O$/(toluene+methanol) molar ratio was about 0.65 and reactor pressure was about 20 psig. Liquid products were collected at about 3-4 hours of run time and were analyzed. The following results, as presented in Tables 5-7. FIG. 5 is a plot of para-xylene selectivity and selectivity for total xylenes for catalysts A-I. FIG. 6 is a plot of para-xylene selectivity and selectivity for total xylenes for catalysts J-O.

TABLE 5

| | Catalyst | | | | | | | | |
|---|---|---|---|---|---|---|---|---|---|
| | A | B | C | D | E | F | G | H | I |
| | | | | | Example | | | | |
| Product Analysis, wt %[1] | 1 | 2 | 3 | 4 | 5 | 6 | 7 | 8 | 9 |
| Water | 21.06 | 21.50 | 21.61 | 21.90 | 19.02 | 18.21 | 16.54 | 17.27 | 21.72 |
| Methanol | 0 | 0.10 | 0.15 | 0.75 | 4.05 | 4.64 | 5.37 | 6.48 | 0.08 |
| Dimethylether | 0 | 0 | 0 | 0 | 0 | 0 | 0 | 0 | 0 |
| Benzene | 1.39 | 1.18 | 0 | 0 | 0 | 0 | 0 | 0 | 0.43 |
| Toluene | 43.82 | 44.77 | 50.54 | 54.86 | 70.21 | 72.00 | 75.33 | 74.11 | 49.63 |
| Ethylbenzene | 0 | 0 | 0 | 0 | 0 | 0 | 0 | 0 | 0 |
| p-Xylene (PX) | 7.11 | 6.85 | 12.35 | 14.30 | 5.58 | 4.49 | 2.65 | 2.03 | 5.86 |
| m-Xylene (MX) | 15.44 | 14.88 | 8.94 | 4.20 | 0.47 | 0.26 | 0.11 | 0.11 | 12.48 |
| o-Xylene (OX) | 6.86 | 6.58 | 3.46 | 1.82 | 0.30 | 0.17 | 0 | 0 | 5.38 |
| Ethyltoluenes | 1.01 | 0.95 | 0.42 | 0.26 | 0.14 | 0.11 | 0 | 0 | 1.18 |
| Trimethylbenzenes | 2.94 | 2.84 | 2.33 | 1.75 | 0.22 | 0.12 | 0 | 0 | 2.81 |
| C10+ | 0.36 | 0.36 | 0.20 | 0.16 | 0 | 0 | 0 | 0 | 0.41 |
| Total Aromatic Products, wt % | 35.11 | 33.64 | 27.70 | 22.49 | 6.71 | 5.15 | 2.76 | 2.14 | 28.55 |
| Total Xylenes, wt % | 29.41 | 28.31 | 24.75 | 20.32 | 6.35 | 4.92 | 2.76 | 2.14 | 23.72 |
| Total Xylenes Selectivity, wt % | 83.77 | 84.16 | 89.35 | 90.35 | 94.63 | 95.53 | 100 | 100 | 83.08 |
| p-Xylene Selectivity, wt % | 24.17 | 24.20 | 49.90 | 70.37 | 87.87 | 91.26 | 96.01 | 94.86 | 24.70 |

[1]Liquid product stream analysis

TABLE 6

| | Catalyst | | | | | |
|---|---|---|---|---|---|---|
| | J | K | L | M | N | O |
| | | | Example | | | |
| Product Analysis, wt %[1] | 10 | 11 | 12 | 13 | 14 | 15 |
| Water | 16.33 | 16.80 | 19.73 | 16.38 | 15.79 | 16.12 |
| Methanol | 0.54 | 0.50 | 2.39 | 1.72 | 2.13 | 0.45 |
| Dimethylether | 0 | 0 | 0 | 0 | 0 | 0 |
| Benzene | 0 | 0 | 0 | 0 | 0 | 0.39 |
| Toluene | 57.02 | 57.76 | 60.57 | 64.47 | 66.10 | 52.37 |
| Ethylbenzene | 0 | 0 | 0 | 0 | 0 | 0 |
| p-Xylene (PX) | 19.55 | 20.18 | 15.05 | 15.24 | 13.37 | 8.54 |
| m-Xylene (MX) | 3.12 | 2.04 | 0.76 | 0.84 | 0.96 | 13.70 |
| o-Xylene (OX) | 1.56 | 1.07 | 0.48 | 0.53 | 0.68 | 5.50 |
| Ethyltoluenes | 0.35 | 0.36 | 0.32 | 0.35 | 0.33 | 0.67 |
| Trimethylbenzenes | 1.39 | 1.17 | 0.45 | 0.47 | 0.55 | 2.05 |
| C10+ | 0.12 | 0.11 | 0.25 | 0 | 0.09 | 0.20 |
| Total Aromatic Products, wt % | 26.09 | 24.93 | 17.31 | 17.43 | 15.98 | 31.05 |
| Total Xylenes, wt % | 24.23 | 23.29 | 16.29 | 16.61 | 15.01 | 27.74 |
| Total Xylenes Selectivity, wt % | 92.87 | 93.42 | 94.11 | 95.30 | 93.93 | 89.34 |
| p-Xylene Selectivity, wt % | 80.69 | 86.65 | 92.39 | 91.75 | 89.07 | 30.79 |

[1]Liquid product stream analysis

TABLE 7

|  | Catalyst | | | |
| --- | --- | --- | --- | --- |
|  | P | Q | R | S |
|  | Example | | | |
| Product Analysis, wt %[1] | 16 | 17 | 18 | 19 |
| Water | 17.65 | 16.46 | 16.22 | 16.58 |
| Methanol | 0.57 | 0.85 | 0.98 | 2.27 |
| Dimethylether | 0 | 0 | 0 | 0 |
| Benzene | 0 | 0 | 0 | 0 |
| Toluene | 56.17 | 60.21 | 61.74 | 66.50 |
| Ethylbenzene | 0 | 0 | 0 | 0 |
| p-Xylene (PX) | 19.87 | 18.17 | 18.34 | 13.34 |
| m-Xylene (MX) | 2.53 | 1.76 | 1.05 | 1.06 |
| o-Xylene (OX) | 1.47 | 0.98 | 0.58 | 0.25 |
| Ethyltoluenes | 0.35 | 0.36 | 0.41 | 0 |
| Trimethylbenzenes | 1.25 | 1.08 | 0.68 | 0 |
| C10+ | 0.13 | 0.12 | 0 | 0 |
| Total Aromatic Products, wt % | 25.60 | 22.47 | 21.06 | 14.65 |
| Total Xylenes, wt % | 23.87 | 20.91 | 19.97 | 14.65 |
| Total Xylenes Selectivity, wt % | 93.24 | 93.06 | 94.82 | 100 |
| p-Xylene Selectivity, wt % | 83.24 | 86.90 | 91.84 | 91.06 |

[1]Liquid product stream analysis

While the invention has been shown in only some of its forms, it should be apparent to those skilled in the art that it is not so limited, but is susceptible to various changes and modifications without departing from the scope of the invention. Accordingly, it is appropriate that the appended claims be construed broadly and in a manner consistent with the scope of the invention.

We claim:

1. A method of modifying a zeolite catalyst, the method comprising:
    contacting a ZSM-5 zeolite having a $SiO_2/Al_2O_3$ mole ratio of from about 200 or more with an aqueous solution of a phosphorus compound; and
    removing water from the phosphorus treated ZSM-5 zeolite; and
    heating the phosphorus treated zeolite at a temperature of 250° C. or higher; and
    wherein the resulting phosphorus treated ZSM-5 zeolite has a $SiO_2/Al_2O_3$ mole ratio of from about 200 or more, a phosphorus content of at least 8% by weight of zeolite and has multiple phosphorus species exhibited by at least three $^{31}P$ MAS NMR peaks with maxima at about 0 ppm to about −50 ppm.

2. The method of claim 1, further comprising:
    subjecting the phosphorus treated zeolite to steaming at a temperature of 350° C. or lower.

3. The method of claim 1, wherein:
    the resulting catalyst has multiple phosphorus species exhibited by at least three $^{31}P$ MAS NMR peaks with maxima at about 0 ppm, about −11 ppm, about −31 ppm or about −44 ppm.

4. The method of claim 1, wherein:
    there are multiple phosphorus species exhibited by at least two $^{31}P$ MAS NMR peaks with maxima at about 0 ppm, about −11 ppm, about −31 ppm or about −44 ppm.

5. The method of claim 1, wherein:
    there are multiple phosphorus species exhibited by $^{31}P$ MAS NMR peaks with maxima at about 0 ppm, about −11 ppm, about −31 ppm and about −44 ppm.

6. The method of claim 1, wherein:
    the phosphorus compound is a phosphorus-containing acid.

7. The method of claim 1, wherein:
    the zeolite has silica/alumina molar ratio of at least 280.

8. The method of claim 1, wherein:
    the zeolite has a silica/alumina molar ratio of at least 200 to 1000.

9. The method of claim 1, wherein:
    phosphorus treated zeolite contains at least one of free phosphate, phosphate bonded to extra-framework Al, AlPO, SAPO and polyphosphate phosphorus species.

10. The method of claim 1, wherein:
    the zeolite has a ratio of framework aluminum to extra-framework aluminum as measured by $^{27}Al$ MAS-NMR of 0.12 to 0.25.

11. The method of claim 1, wherein:
    the ZSM-5 zeolite is contacted with the aqueous solution of the phosphorus compound by forming a slurry of the ZSM-5 zeolite and the aqueous solution of the phosphorus compound.

12. The method of claim 1, wherein:
    the phosphorus content of the zeolite is provided without deposition of phosphorus onto the catalyst by organophosphorus vapor deposition.

13. A method of modifying a zeolite catalyst, the method comprising:
    contacting a ZSM-5 zeolite having a $SiO_2/Al_2O_3$ mole ratio of from about 200 or more with an aqueous solution of a phosphorus compound; and
    removing water from the phosphorus treated ZSM-5 zeolite; and
    heating the phosphorus treated zeolite at a temperature of 250° C. or higher and steaming the phosphorus treated zeolite at a temperature of 350° C. or lower; and
    wherein the phosphorus treated ZSM-5 zeolite has a $SiO_2/Al_2O_3$ mole ratio of from about 200 or more, a phosphorus content of at least 8% by weight of zeolite and has multiple phosphorus species exhibited by at least three $^{31}P$ MAS NMR peaks with maxima at about 0 ppm to about −50 ppm.

14. The method of claim 13, wherein:
    the resulting catalyst has multiple phosphorus species exhibited by at least three $^{31}P$ MAS NMR peaks with maxima at about 0 ppm, about −11 ppm, about −31 ppm or about −44 ppm.

15. The method of claim 13, wherein:
    there are multiple phosphorus species exhibited by at least two $^{31}P$ MAS NMR peaks with maxima at about 0 ppm, about −11 ppm, about −31 ppm or about −44 ppm.

16. The method of claim 13, wherein:
    there are multiple phosphorus species exhibited by $^{31}P$ MAS NMR peaks with maxima at about 0 ppm, about −11 ppm, about −31 ppm and about −44 ppm.

17. The method of claim 13, wherein:
    the phosphorus compound is a phosphorus-containing acid.

18. The method of claim 13, wherein:
    the zeolite has silica/alumina molar ratio of at least 280.

19. The method of claim 13, wherein:
    the zeolite has a silica/alumina molar ratio of at least 200 to 1000.

20. The method of claim 13, wherein:
    phosphorus treated zeolite contains at least one of free phosphate, phosphate bonded to extra-framework Al, AlPO, SAPO and polyphosphate phosphorus species.

21. The method of claim 13, wherein:
the zeolite has a ratio of framework aluminum to extra-framework aluminum as measured by $^{27}$Al MAS-NMR of 0.12 to 0.25.

22. The method of claim 13, wherein:
the ZSM-5 zeolite is contacted with the aqueous solution of the phosphorus compound by forming a slurry of the ZSM-5 zeolite and the aqueous solution of the phosphorus compound.

23. The method of claim 13, wherein:
the phosphorus content of the zeolite is provided without deposition of phosphorus onto the catalyst by organophosphorus vapor deposition.

\* \* \* \* \*